United States Patent
Dees, Jr.

(10) Patent No.: US 7,451,550 B2
(45) Date of Patent: Nov. 18, 2008

(54) ROTATIONAL ALIGNMENT FEMORAL SIZING GUIDE

(75) Inventor: Roger Ryan Dees, Jr., Senatobia, MS (US)

(73) Assignee: Smith & Nephew, Inc., Memphis, TN (US)

( * ) Notice: Subject to any disclaimer, the term of this patent is extended or adjusted under 35 U.S.C. 154(b) by 357 days.

(21) Appl. No.: 11/316,260

(22) Filed: Dec. 21, 2005

(65) Prior Publication Data

US 2006/0142778 A1 Jun. 29, 2006

Related U.S. Application Data

(60) Provisional application No. 60/638,153, filed on Dec. 21, 2004.

(51) Int. Cl.
*A61B 17/58* (2006.01)
*A61B 1/00* (2006.01)

(52) U.S. Cl. .......................... 33/512; 606/88

(58) Field of Classification Search ........... 33/511–512; 606/88, 102
See application file for complete search history.

(56) References Cited

U.S. PATENT DOCUMENTS

| | | | |
|---|---|---|---|
| 4,487,203 A | 12/1984 | Androphy | |
| 5,275,603 A | 1/1994 | Ferrante | |
| 5,364,401 A | 11/1994 | Ferrante et al. | |
| 5,486,178 A | 1/1996 | Hodge | |
| 5,624,444 A | 4/1997 | Wixon | |
| 5,683,397 A | 11/1997 | Vendrely et al. | |
| 5,776,137 A | 7/1998 | Katz | |
| 5,830,216 A | 11/1998 | Insall et al. | |
| 6,013,081 A | 1/2000 | Burkinshaw et al. | |
| 6,096,043 A | 8/2000 | Techiera et al. | |
| 6,106,529 A | 8/2000 | Techiera | |
| 6,110,200 A * | 8/2000 | Hinnenkamp ................. 33/512 |
| 6,290,704 B1 | 9/2001 | Burkinshaw et al. | |
| 6,458,135 B1 | 10/2002 | Harwin et al. | |
| 6,673,077 B1 | 1/2004 | Katz | |
| 7,261,719 B1 * | 8/2007 | Twomey et al. ............. 606/102 |
| 7,299,561 B2 * | 11/2007 | Castaneda .................... 33/512 |
| 2003/0153924 A1 * | 8/2003 | Kana et al. .................... 606/89 |
| 2004/0215205 A1 | 10/2004 | Plumet et al. | |
| 2004/0220583 A1 | 11/2004 | Pieczynski | |

(Continued)

FOREIGN PATENT DOCUMENTS

EP 0 556 998 B1 6/1997

(Continued)

OTHER PUBLICATIONS

International Search Report in related Application No. PCT/US2005/046863 Apr. 27, 2006.

*Primary Examiner*—Yaritza Guadalupe-McCall
(74) *Attorney, Agent, or Firm*—Kilpatrick Stockton LLP (57) ABSTRACT

Embodiments of the present invention allow unlimited rotational alignment between two boundaries for alignment with anatomic landmarks while still referencing both posterior condyles for A/P sizing of the distal femur. In particular embodiments, the system provides at least one movable paddle that provides a reference point from the condyles so that the measuring assembly can be aligned to be parallel with the epicondylar axis. Once the measuring assembly is properly angled, the A/P length of the bone can then be measured from a proper reference point.

15 Claims, 6 Drawing Sheets

U.S. PATENT DOCUMENTS

| | | |
|---|---|---|
| 2005/0049603 A1 | 3/2005 | Calton |
| 2005/0149042 A1* | 7/2005 | Metzger ..................... 606/88 |
| 2005/0209600 A1 | 9/2005 | Fencl |
| 2006/0179979 A1* | 8/2006 | Dees, Jr. ..................... 600/587 |

FOREIGN PATENT DOCUMENTS

| | | |
|---|---|---|
| EP | 0 720 834 B1 | 6/1999 |
| EP | 1 013 231 A2 | 6/2000 |
| EP | 1 013 231 A3 | 6/2000 |
| EP | 1302 167 A2 | 4/2003 |
| EP | 1302 167 A3 | 4/2003 |
| WO | WO 96/01588 A1 | 1/1996 |
| WO | WO 96/25114 A1 | 8/1996 |
| WO | WO 00/13594 A1 | 3/2000 |
| WO | WO 2005/046432 A2 | 5/2005 |

* cited by examiner

ROTATIONAL ALIGNMENT FEMORAL SIZING GUIDE

This application claims the benefit of U.S. Provisional Patent Application Ser. No. 60/638,153 filed Dec. 21, 2004 titled "Rotational Alignment Femoral Sizing Guide," the entire contents of which are hereby incorporated by reference.

FIELD OF THE INVENTION

The present invention relates to a sizing and rotational alignment apparatus for determining the anterior-posterior size of a distal end of a femur in order to determine the proper implant size, and to methods for using such an apparatus.

BACKGROUND

In total knee joint replacement surgery or arthroplasty, the knee joint is replaced with an artificial implant. The implant typically includes a tibial component, a femoral component, and a mobile bearing insert (a patella component).

Most femoral components have an inner surface with intersecting flat surfaces that interface with a surgically prepared distal femoral surface. The outer surface typically has a curvature that faces a corresponding tibial component attached to the patient's tibia. Two curved condylar regions on the femoral component replicate the natural femoral condyles.

Determining the proper anterior/posterior (A/P) size of the distal femur is a difficult procedure. The surgeon must measure the correct A/P size of the distal femur, while setting rotational alignment to anatomic landmarks (e.g., epicondylar axis and the A/P axis). The A/P femoral size is usually derived from the distance between the posterior condyles and the anterior cortex of the distal femur. The rotational alignment (rotation on a transverse plane at the distal face of the femur) is usually derived from anatomic landmarks. This rotational alignment, however, is typically not in perpendicular/parallel relation or at a set angle to the A/P measurement plane needed to properly size the distal femur. Accordingly, it is not as easy as measuring from the back (posterior) to the front (anterior) of the bone and choosing an implant.

Instruments used for this sizing in the past have included two stationary paddles that are placed vertically against the posterior surface of a resected distal femur. These instruments do not account for or measure rotational alignment between two boundaries (for alignment with anatomic landmarks), while still referencing both posterior condyles to determine the proper A/P size of the distal femur. Stationary paddles also do not account for condyles of different sizes and shapes (e.g., one condyle may extend further than another due to patient irregularity or diseased tissue).

However, instruments that address each variable (rotation and size) independently increase procedural time and, more importantly, can result in less than optimal A/P sizing. For example, the use of two different instruments prevents the sizing from being measured in relation to the rotational location being used. Specifically, the sizing is not measured perpendicular to the rotational location being used.

Some instruments do measure both rotational alignment and A/P sizing simultaneously. However, these instruments lack adjustment, so that when they are rotated with respect to the anatomic landmarks, they only reference one posterior condyle. (Again, a precise measurement is not obtainable because one condyle may extend further than another due to patient irregularity or diseased tissue or any other reason.) In other cases, the instruments have additional components that can be added to the instrument to substitute for condylar contact, but these additional components are in increments that limit adjustability and can add to surgical procedure time because they need to be interchanged to determine "best fit" scenarios.

Accordingly, there is a need to provide a femoral sizing guide that measures and correlates both (1) rotational alignment (the rotation at the distal face of the femur) and A/P sizing.

SUMMARY

Embodiments of the present invention allow unlimited rotational alignment between two boundaries for alignment with anatomic landmarks while still referencing both posterior condyles for A/P sizing of the distal femur. In particular embodiments, the system provides at least one movable paddle that provides a reference point from the condyles so that the measuring assembly can be aligned to be parallel with the epicondylar axis. Once the measuring assembly is properly angled, the A/P length of the bone can then be measured from a proper reference point.

DETAILED DESCRIPTION OF THE DRAWINGS

Figure 1:
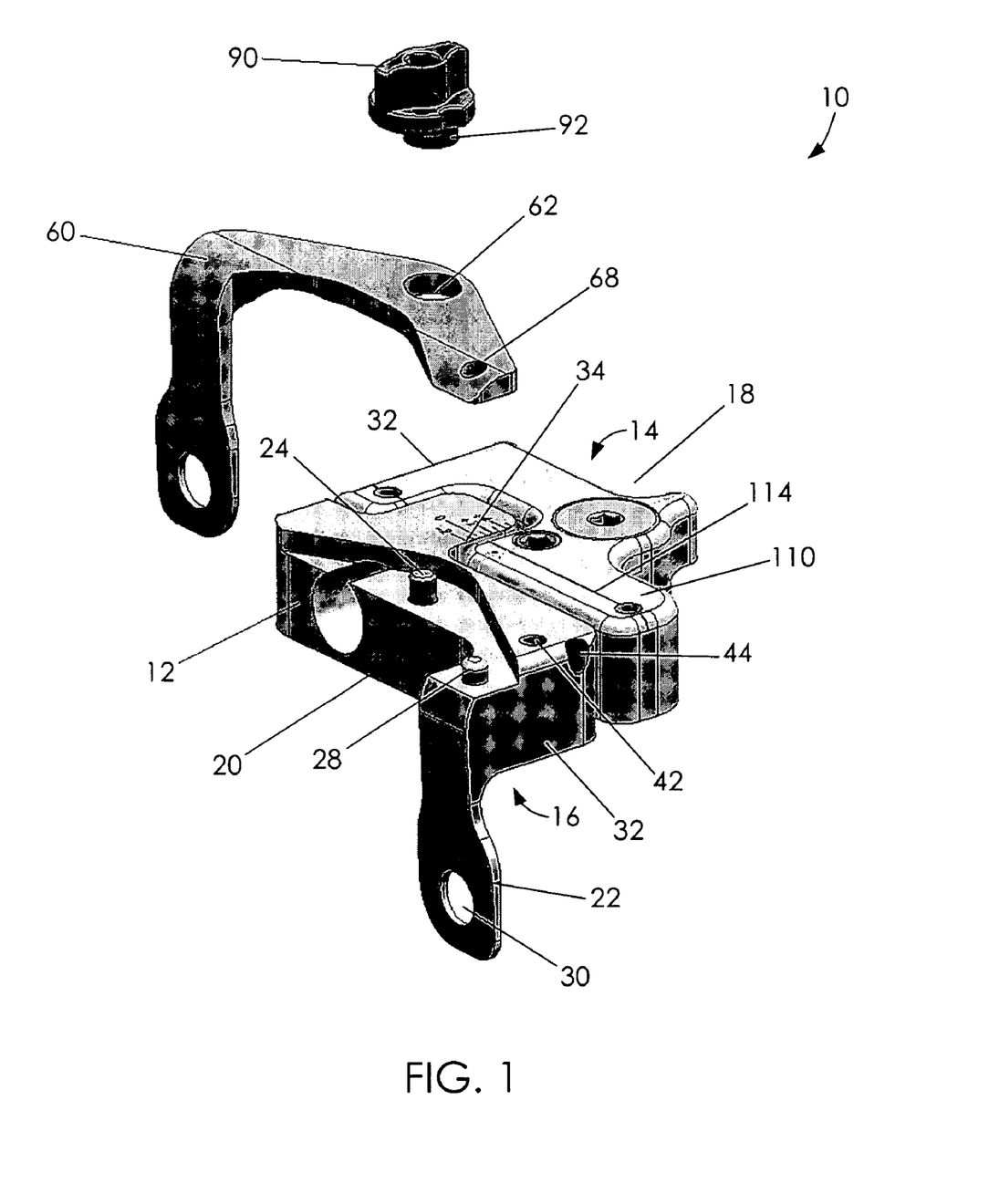
FIG. 1 shows an exploded perspective view of an assembly according to one embodiment of the invention.

FIG. 1 shows a body 12, a movable paddle 60, and a rotational actuator 90, collectively referred to as assembly 10. The body 12 is a block with an upper surface 14, a lower surface 16, an anterior portion 18, and a posterior portion 20. (These anatomical directional components are intended to refer to body 12 when it is in place on a distal resected femur.) Extending from posterior portion is a first paddle 22. This paddle 22 is intended to provide a stable condylar reference point for body 12. Paddle 22 is also shown having a fixation portion 30, which is intended to receive a fixation pin, screw, or any other securing mechanism to secure paddle 22 in place. (Although this first paddle 22 is provided in preferred embodiments of the invention, it is not essential for the assembly 10 to function as desired.)

Upper surface 14 of body 12 has an actuator member 24. Actuator member 24 is located toward the posterior portion of the body and substantially midway between either side 32 of body 12. Although member 24 is shown as a protruding pin, it should be understood that it could be an indentation, dimple, or any other feature of any shape and size that will allow body 12 to cooperate with a second paddle, described more below.

Body 12 also features a pivot member 28. As with actuator member 24, pivot member 28 is shown as a protruding pin, but it should be understood that it could be an indentation, dimple, or any other feature of any shape and size that will allow a pivoting motion to occur between a second paddle and body 12.

Body 12 is also shown having sizing indicia 34. In a preferred embodiment, the indicia are at 1 mm intervals, although other intervals are possible.

Figure 5:
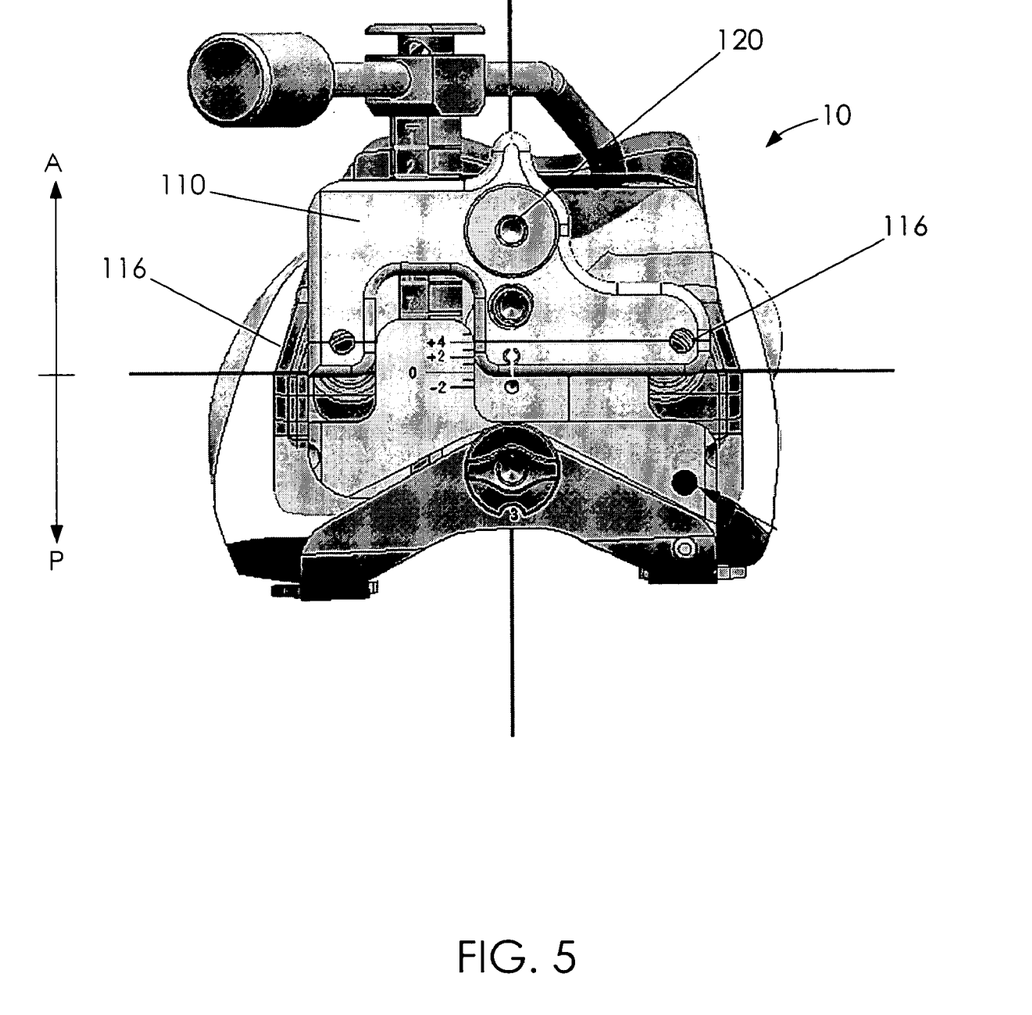
FIG. 5 shows the assembly of FIG. 3 being used to measure the A/P length of the femur.
Figure 6:
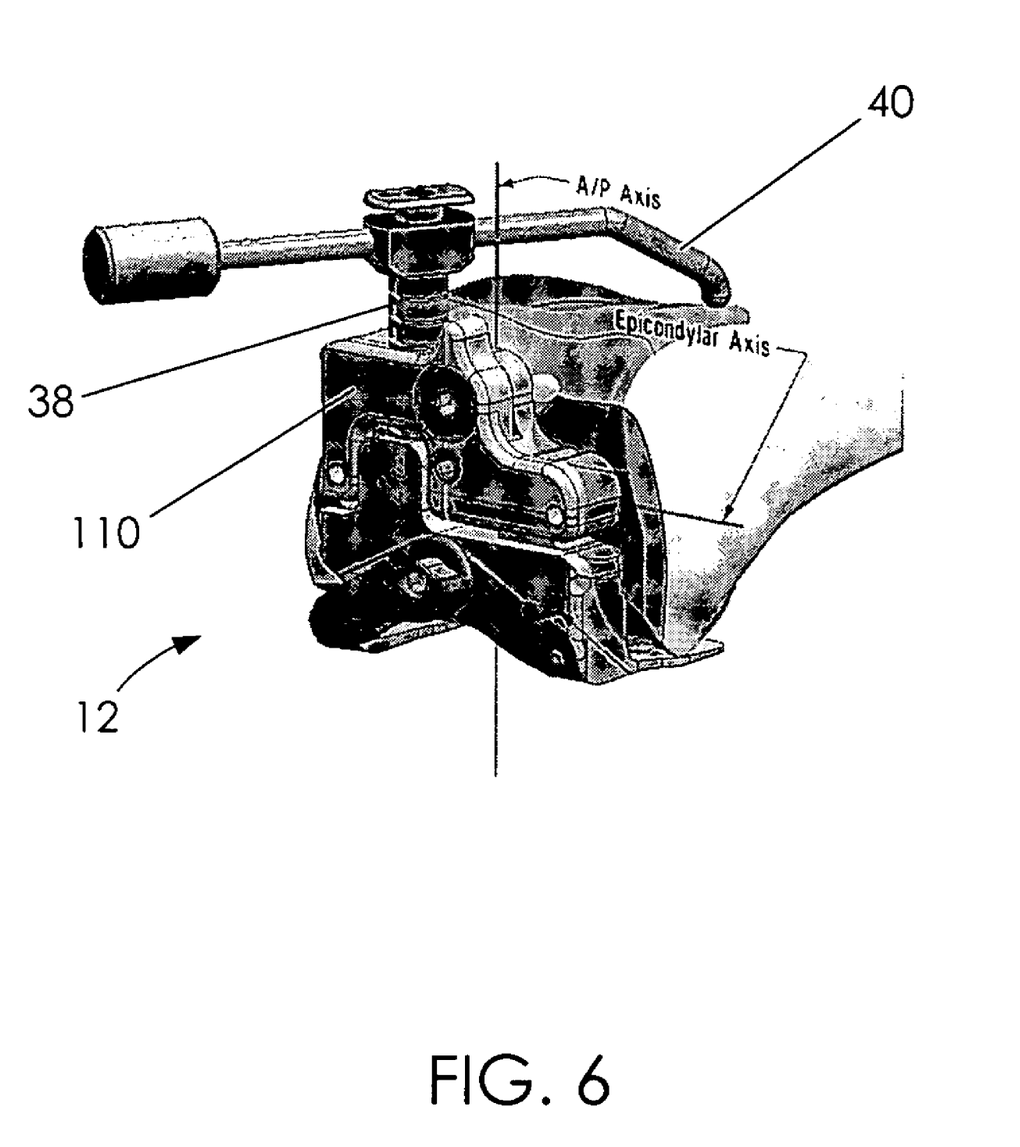
FIG. 6 shows a side perspective view of the assembly of FIGS. 3-5.

Body 12 further has a shiftable measuring member 110. In some embodiments, member 110 is on a track 38 that cooperates with stylus 40, as shown in FIG. 6, although it may cooperate with body in any other way. In a particularly preferred embodiment, measuring member 110 is a separate portion that is adjusted by member 120, as shown in FIG. 5. Member 120 may be a cam portion that is rotated, it may be an indentation that receives a hex driver, it may be a raised pin that is turned, it may be a threaded or lead screw, or any other type of adjustment appropriate for the measuring described below. As shown in more detail by FIG. 2, member 110 preferably has a mark 114 on its upper surface 112 indicating the epicondylar axis 140, shown in FIG. 3. Mark 114 is preferably aligned with a zero-mark 36 on the sizing indicia 34 of the body 12.

As will be described in more detail below, once the proper rotation is determined using paddles to align body 12 to be parallel or at least substantially parallel with the epicondylar axis, the measuring member 110 is used to determine the proper A/P size of the distal femur. Member 110 is movable in the anterior and posterior direction (shown by the A/P axis 142, in FIG. 3) with respect to body 12.

Referring back to FIG. 1, second paddle 60 is shown as an L-shaped member that is adapted to cooperate with body 12 via an actuator member 62. In use, actuator member 62 is intended to associate with actuator member 24. Although cooperator 62 is shown as an opening, hole, or slot, it should be understood that it could be a protruding pin or any other feature of any shape and size that will allow member 60 to cooperate with body 12.

Second paddle 60 also has a pivot member 68. Pivot member 68 works with pivot member 28 of body 12. Although pivot member 68 is shown as an opening, hole, or slot, it should be understood that it could be a protruding pin or any other feature of any shape and size that will allow member 68 to cooperate with body 12.

Rotational actuator 90 is has a cam member 92 that cooperates with actuator member 24 and actuator member 62 to measure the rotational alignment of the condyles (or any other desired anatomical reference point, in this example and description, the condyles are the reference points being used, but it should be understood that it is possible to use other anatomical reference points).

In use, the second paddle 60 is assembled onto the body 12 by aligning the pivot members 68 and 28 together and the actuator member 24 and actuator member 62 together. The rotational actuator 90 is then assembled to cooperate with the member 24 and/or cooperator 62. A screw may be used to make this connection if these portions are both openings or indentations. If the actuator member 24 is a pin, as shown, then the pin may cooperate with an opening in rotational actuator 90, if desired. The completed device is assembly 10, shown in FIG. 2.

It is worth noting here that two paddles are not required, and that the one or more paddles do not necessarily have to extend to the posterior condyles. In other words, one paddle may be used while the other side is left off, although it is preferable for the paddle that is provided to be rotatable. If one of the paddles is left off, the surgeon usually prefers a visual posterior reference, and any type of reference may be provided. In some instances, a paddle may be machined off of the body member with a visual reference created by the posterior edge of what is left. In other embodiments, there may be an arrow where the stationary paddle would be. In sum, two posterior paddles are not a necessity as long as both posterior condyles (or epicondyles, or two other planer points) are referenced via contact or visual reference.

Figure 2:
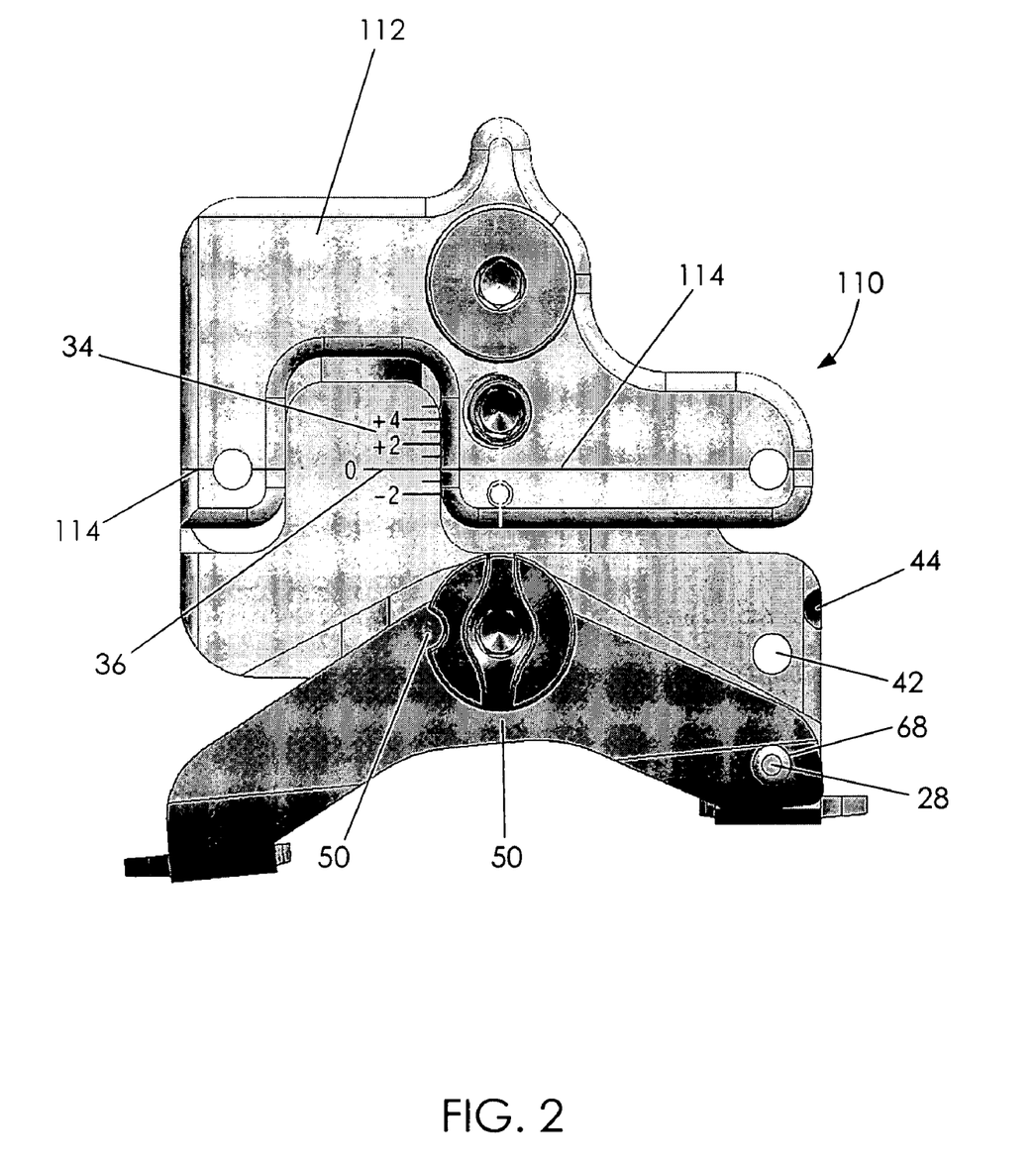
FIG. 2 shows the embodiment of FIG. 1 in an assembled position.

Device 10 also has degree or angle markings 50. These markings 50 may be provided on paddle 60, as shown in FIG. 2, or they may be provided on body 12, rotational actuator 90, an anywhere else that allows markings 50 to be easily read when the actuator 90 is activated. Markings 50 are intended to show how many degrees the body 12 needed to be rotated in order to be parallel to the epicondylar axis 140.

In use, assembly 10 is placed on the resected distal femur (which is the preferable method, although it may be possible to use assembly 10 without resecting the femur). Body 12 is slid or rotated anteriorly until both posterior paddles 22, 60 are in contact with the posterior condyles of the distal femur. While maintaining contact of the paddles 22, 60 with the femoral-posterior condyles, the rotational actuator 90 is turned until the desired rotational alignment is achieved. When turned, the rotational actuator 90 causes cam 92 to move second paddle 60 radially about a pivot axis defined by pivot members 28, 68. Alternatively, actuator 90 could move body with response to paddle 60.

Figure 3:
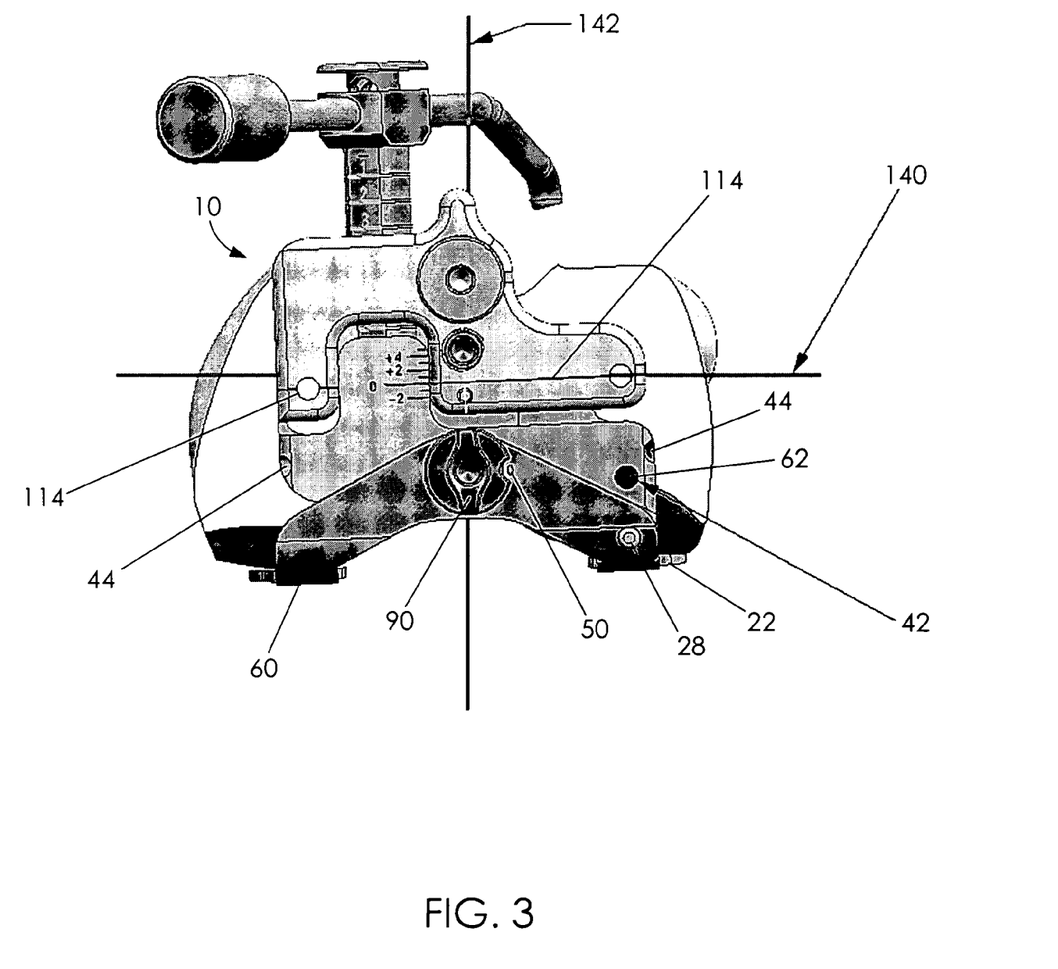
FIG. 3 shows a top plan view of an assembly according to one embodiment of the invention in place on a patient's femur, prior to activation of the cam assembly.

A specific example will now be described for clarity, but it is not intended to be a limiting description of the uses or structures defined herein. FIG. 3 shows assembly 10 in place on a patient's resected femur. Paddles 22, 60 are in contact with the posterior portion of the patient's condyles. Paddle 60 cooperates with body 12 via pivot members 28, 68. Rotational actuator 90 is secured in place. In FIG. 3, the assembly is shown as not being oriented at any angle, because marking reads "0".

Figure 4:
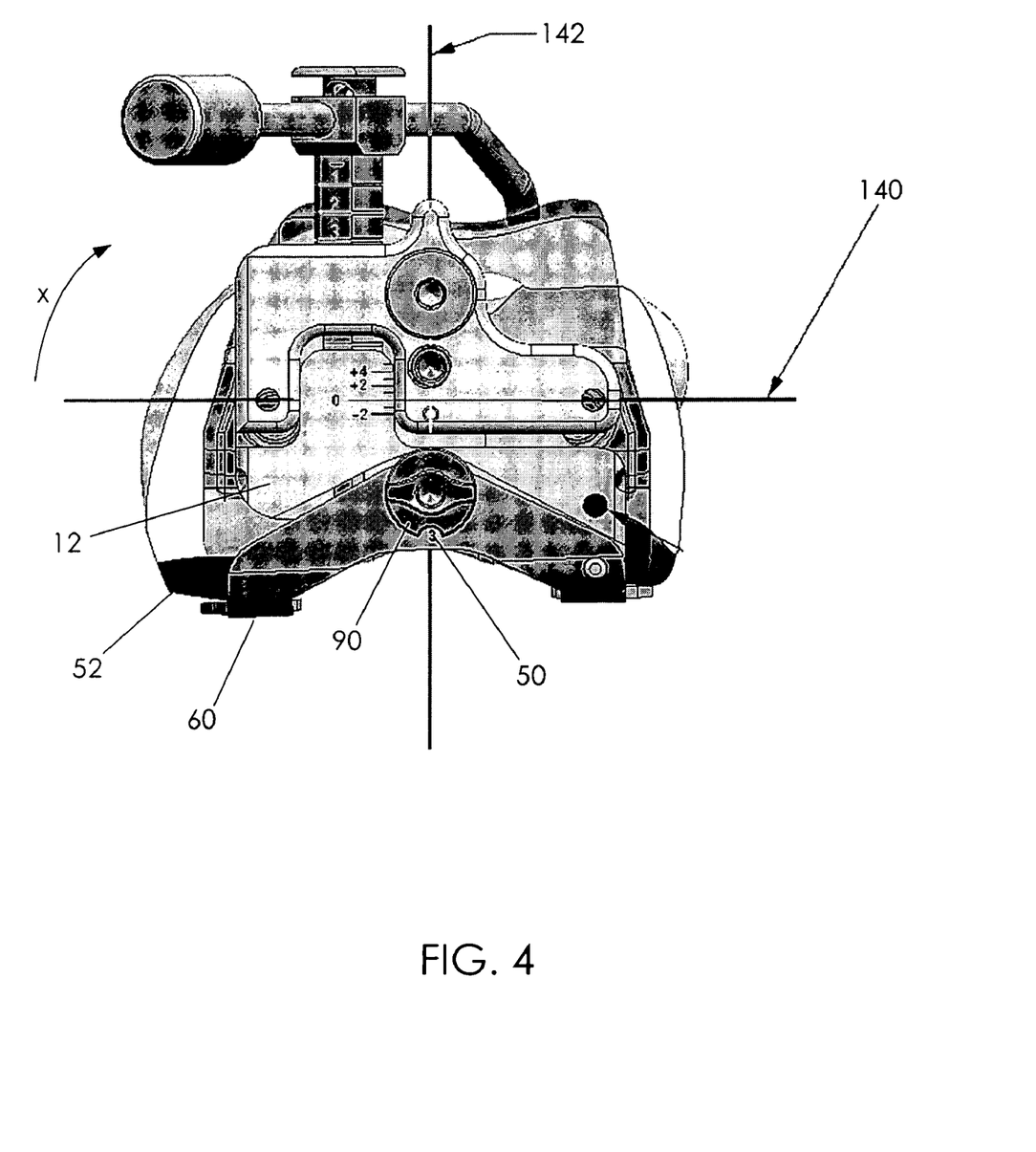
FIG. 4 shows the assembly of FIG. 3 in place, once the cam has been activated and in the process of measurement.

As rotational actuator 90 is turned (in this example, it is turned clockwise, but it should be understood that any rotational method or direction may be used), the body 12 is rotated slightly, as shown by arrow X in FIG. 4. FIG. 4 shows an example where body 12 is rotated 3°, as shown by marking 50 and indicated by the space 52 created between paddle 60 and body 12. It can also be seen that, in this example, the mark 114 is even with the epicondylar axis 140, so proper rotational alignment has been reached. In the example, shown in FIG. 2, proper rotational alignment is reached at 6°. Mark 114 is just one example of an indicia that may be used to determine when rotational alignment has been reached, and it should be understood that other options are possible.

It should also be noted that markings 50 are shown in 3° intervals for the sake of example only. They could be provided in any increment desired, such as degree by degree, half degrees, and so forth. It should also be understood that if millimeters or some other measurement was desired instead of degrees, that option is within the scope of this invention.

As described, this rotational adjustment allows the body 12 to be rotationally aligned to the patient's anatomy. An optional rotational fixation hole 42 can provided to receive a fixation pin to aid in maintaining posterior paddle 22/condylar contact. Once rotational alignment is achieved, fixation pins can be inserted through the fixation holes 44 to fixate the assembly 10 to the distal femur in the proper rotational alignment position.

Then, the A/P sizing is performed using the measuring member 110. As shown in FIG. 5, measuring member 110 is adapted to expand assembly 10 anteriorly or contract it posteriorly (shown by arrows "A" and "P"). One way such measuring movement may be achieved is via member 120 on measuring member 110, although many other options are possible and considered within the scope of various embodiments of this invention. If provided, drill guide holes 116 in the measuring member 110 are used to place the distal-femoral resection guides (various forms of which are known in the art and used as cutting blocks to prepare the patient's femur to receive an implant.) The drill guide holes 116 provide a scaffold through which a drill can extend and prepare holes in the distal femur at the appropriate location in order to provide location reference marks for the cutting block to be used.

In an alternate embodiment, both first and second paddles may be movable and/or rotatable. They may both be separate pieces and communicate with a mating pivot post or they may have separate mating pivot posts.

Additionally, although the paddle(s) have been described as preferably actuated via a cam mechanism, the paddles could be actuated in any number of ways, for example, they may be gear-driven, driven via a radial slot with a lock, threaded or lead screw actuated, variable angled inserts or modules, or via any other appropriate method.

Changes and modifications, additions and deletions may be made to the structures and methods recited above and shown in the drawings without departing from the scope or spirit of the invention and the following claims.

What is claimed is:

1. A rotational alignment femoral sizing guide assembly, comprising:
   (a) a body comprising an upper surface, a lower surface, an anterior portion, a posterior portion, and an actuator member located on the upper surface of the body;
   (b) a stable condylar reference point or member on the body;
   (c) a movable condylar referencing member having an actuator member cooperating portion that cooperates with the actuator member of the body; and
   (d) a rotational actuator that cooperates with the actuator member of the body and the actuator member cooperating portion of the movable condylar referencing member to provide varying degrees of angulation between the movable condylar referencing member and the body, wherein the stable condylar reference point or member on the body and the movable condylar reference member reference independently from one another.

2. The assembly of claim 1, further comprising a measuring member that cooperates with the body via a member adapted to move the measuring member with respect to the body in order to measure an anterior/posterior distance.

3. The assembly of claim 1, wherein the movable condylar referencing member is adapted to pivot away from and toward the body.

4. The assembly of claim 1, wherein the movable condylar referencing member comprises a pivot member that cooperates with a pivot member of the body.

5. The assembly of claim 1, further comprising angle markings on the movable condylar referencing member, the body, or the rotational actuator, wherein the rotational actuator is adapted to pivot the body to an angle that is marked by the angle markings.

6. The assembly of claim 1, wherein the body has sizing indicia on its upper surface.

7. The assembly of claim 1, wherein the body comprises one or more fixation holes.

8. The assembly of claim 1, further comprising a measuring member that cooperates with the body and is adapted to be extended toward the anterior or posterior portion of the body in order to determine what size prosthesis should be used.

9. The assembly of claim 8, wherein the measuring member comprises a mark to indicate an axis.

10. The assembly of claim 8, wherein the measuring member comprises one or more drill guide holes.

11. The assembly of claim 1, wherein the stable condylar reference point or member or the movable condylar referencing member or both have one or more fixation portions for securement to bone.

12. A method for measuring the rotation and size of a bone area, comprising:
   (a) providing an assembly comprising a body with a stable condylar reference member and a movable condylar referencing member adapted to cooperate with the body via an actuator, wherein the stable condylar reference point or member and the movable condylar reference member reference independently from one another, further comprising angle measuring markings located on one or more of the body, the one or more condylar referencing members, or the actuator;
   (b) placing the assembly on the bone to be measured; and
   (c) actuating the actuator to cause the body to rotate with respect to a reference point marked by the movable condylar referencing member.

13. The method of claim 12, wherein the assembly further comprises a measuring member adapted to cooperate with the body, the method further comprising:
   (d) adjusting a location of the measuring member to measure the width, length, or depth of the bone area to be measured.

14. The method of claim 13, further comprising:
   (e) correlating an implant size to the measurements taken.

15. The method of claim 12, further comprising:
   (d) reading an angle measured by the angle measuring markings.

* * * * *